(12) United States Patent
Dodrill

(10) Patent No.: US 11,903,747 B2
(45) Date of Patent: Feb. 20, 2024

(54) BREATHABLE PACKAGE WITH COHESIVE COLOR HEAT SEAL INDICATOR

(71) Applicant: PAXXUS, INC., Addison, IL (US)

(72) Inventor: Doug Dodrill, Addison, IL (US)

(73) Assignee: Paxxus, Inc., Addison, IL (US)

( * ) Notice: Subject to any disclaimer, the term of this patent is extended or adjusted under 35 U.S.C. 154(b) by 38 days.

(21) Appl. No.: 17/679,828

(22) Filed: Feb. 24, 2022

(65) Prior Publication Data

US 2022/0280256 A1   Sep. 8, 2022

Related U.S. Application Data

(60) Provisional application No. 63/156,577, filed on Mar. 4, 2021.

(51) Int. Cl.
| | |
|---|---|
| *A61B 50/30* | (2016.01) |
| *B65D 75/30* | (2006.01) |
| *B65D 75/52* | (2006.01) |
| *B65D 79/02* | (2006.01) |

(52) U.S. Cl.
CPC .............. *A61B 50/30* (2016.02); *B65D 75/30* (2013.01); *B65D 75/52* (2013.01); *B65D 79/02* (2013.01); *A61B 2050/314* (2016.02)

(58) Field of Classification Search
CPC ......... A61B 50/30; B65D 75/30; B65D 75/52
USPC ................................... 206/484, 484.1, 484.2
See application file for complete search history.

(56) References Cited

U.S. PATENT DOCUMENTS

| | | | | |
|---|---|---|---|---|
| 4,874,090 A | * | 10/1989 | Dyke | A61B 50/30 |
| | | | | 206/439 |
| 6,622,864 B1 | * | 9/2003 | Debbs | A61B 50/30 |
| | | | | 206/363 |
| 6,629,602 B1 | * | 10/2003 | Heyman | A61L 2/07 |
| | | | | 206/484.1 |
| 6,821,587 B2 | * | 11/2004 | Forbes | B01J 20/28016 |
| | | | | 206/524.1 |
| 8,689,976 B2 | * | 4/2014 | Wittrock | A61B 50/30 |
| | | | | 206/459.1 |
| 2014/0120292 A1 | * | 5/2014 | Dodrill | B29D 99/0053 |
| | | | | 428/41.6 |
| 2014/0346071 A1 | * | 11/2014 | Genosar | A61J 1/067 |
| | | | | 206/438 |
| 2018/0162619 A1 | * | 6/2018 | Kocur | B65D 5/54 |
| 2019/0143642 A1 | * | 5/2019 | Johnson | B32B 27/18 |
| | | | | 428/339 |
| 2020/0270037 A1 | * | 8/2020 | Yasuda | B65D 75/36 |
| 2022/0041356 A1 | * | 2/2022 | Peterson | B32B 7/12 |

* cited by examiner

FOREIGN PATENT DOCUMENTS

| | | |
|---|---|---|
| EP | 2911874 A1 | 9/2015 |
| GB | 2323812 A | 10/1998 |

OTHER PUBLICATIONS

European Search Report for corresponding Application No. 22159423.7 dated Jul. 28, 2022, 6 pages.

*Primary Examiner* — Jacob K Ackun

(74) *Attorney, Agent, or Firm* — Seyfarth Shaw LLP

(57) ABSTRACT

A breathable package that allows a device or object disposed in the package to be sterilized, and maintains the sterile condition until the package is opened at the point of use. The package also provides a visual indication that the package seal integrity has not been compromised or that the package has been compromised or breached. The package includes a first material, such as a film, and a second non-woven material, such as non-woven high density polyethylene, that form opposing sides of the package.

17 Claims, 4 Drawing Sheets

BREATHABLE PACKAGE WITH COHESIVE COLOR HEAT SEAL INDICATOR

CROSS REFERENCES TO RELATED APPLICATIONS

This application claims the benefit of U.S. Provisional Patent Application Ser. No. 63/156,577, filed Mar. 4, 2021, the contents of which is incorporated herein by reference in its entirety.

TECHNICAL FIELD OF THE INVENTION

The present invention relates to package sealing elements.

BACKGROUND OF THE INVENTION

Sterilized packaging for the delivery of medical devices and components is a critical element of the healthcare system. Many technologies exist for the sterilization of these products including irradiation, heat, and sterilant gases. For the sterilant gas approach, a package design is required that allows the gas to enter the fully sealed package and then be evacuated from the package after the sterilization exposure is complete. At the same time, the package has to prevent the ingress of microbes, viruses, and bacteria. This is commonly accomplished through the use of a breathable non-woven polymeric material on one or more sides of the package, and the package is sealed by applying heat and/or pressure resulting in chemical and mechanical bonding.

Increased attention to patient safety and infection prevention has prompted enhanced regulatory expectations regarding package integrity and sterility. Specifically, the ability to clearly confirm package integrity by the user at the point of use (such as a doctor or nurse in a hospital or medical office) is required.

However, current gas sterilizable packaging does not provide any robust visual evidence of seal integrity. In the event that the user cannot confirm the presence of the intended seal, the contents of the package may be used in an unsafe condition. In addition, traditional packages containing a non-woven material are often prone to the generation of loose fibers during the opening process. These loose fibers are considered a patient safety risk in critical hospital settings.

SUMMARY OF THE INVENTION

In the medical field, devices or objects delivered in a sterile state are to be designed, manufactured and packaged in accordance with appropriate procedures to ensure that they are sterile when placed on the market and that they remain sterile, under the transport and storage conditions specified by the manufacturer, until that packaging is verified and opened at the point of use.

The present invention relates broadly to a breathable package that allows a device or object disposed in the package to be sterilized, and maintains the sterile condition until the package integrity is verified and the package opened at the point of use. The package provides a bold visual indication of seal integrity and allows the seal to be opened without the generation of loose fibers. The package includes a first material, such as a film, and a second non-woven material, such as non-woven high density polyethylene, that form opposing sides of the package. A pigmented cohesive peel layer is disposed between the first and second materials. In a closed configuration, the package is sealed, with the adhesive layer coupled to the first material and the pigmented cohesive peel layer coupled to the adhesive layer and the second material. In an open configuration, the package is open, with the adhesive layer remaining coupled to the first material, and the pigmented peel layer substantially separated from the adhesive layer and coupled to the second material.

BRIEF DESCRIPTION OF THE DRAWINGS

For the purpose of facilitating an understanding of the subject matter sought to be protected, there is illustrated in the accompanying drawing embodiments thereof, from an inspection of which, when considered in connection with the following description, the subject matter sought to be protected, its construction and operation, and many of its advantages, should be readily understood and appreciated.

DETAILED DESCRIPTION

Figure 1:
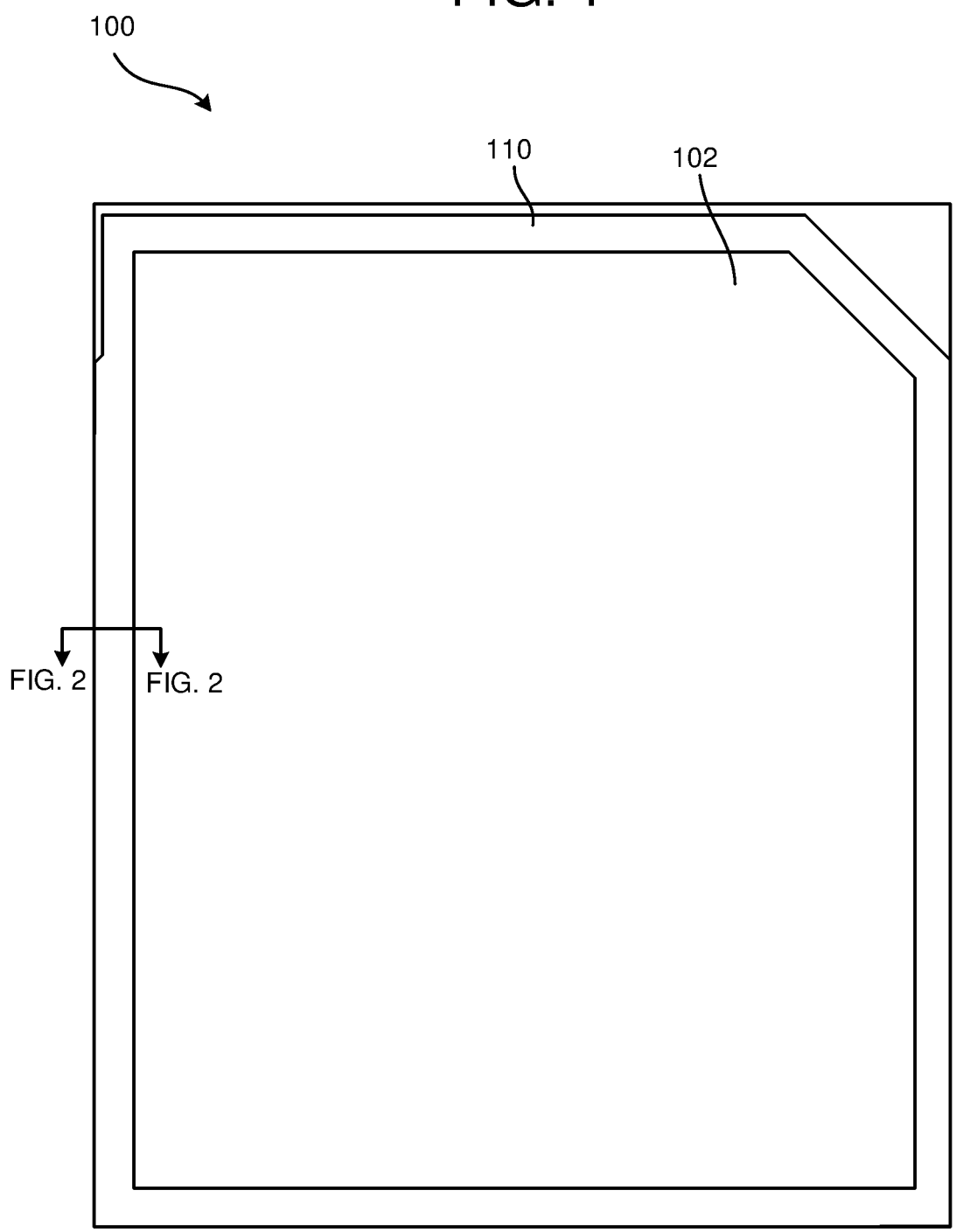
FIG. 1 is a side view of a package in a closed configuration, according to an embodiment of the present invention.

While this invention is susceptible of embodiments in many different forms, there is shown in the drawings, and will herein be described in detail, a preferred embodiment of the invention with the understanding that the present disclosure is to be considered as an exemplification of the principles of the invention and is not intended to limit the broad aspect of the invention to embodiments illustrated. As used herein, the term "present invention" is not intended to limit the scope of the claimed invention and is instead a term used to discuss exemplary embodiments of the invention for explanatory purposes only.

The present invention relates broadly to a breathable package that allows a device or object disposed in the package to be sterilized, and maintains the sterile condition until the package integrity is verified and the package opened at the point of use. The package provides a bold visual indication of seal integrity and allows the seal to be opened without the generation of loose fibers. The package includes a first material, such as a film, and a second non-woven material, such as non-woven high density polyethylene, that form opposing sides of the package. A pigmented cohesive peel layer is disposed between the first and second materials. In a closed configuration, the package is sealed, with the adhesive layer coupled to the first material and the pigmented cohesive peel layer coupled to the adhesive layer and the second material. In an open configuration, the package is open, with the adhesive layer remaining coupled to the first material, and the pigmented peel layer substantially separated from the adhesive layer and coupled to the second material.

Figure 2:
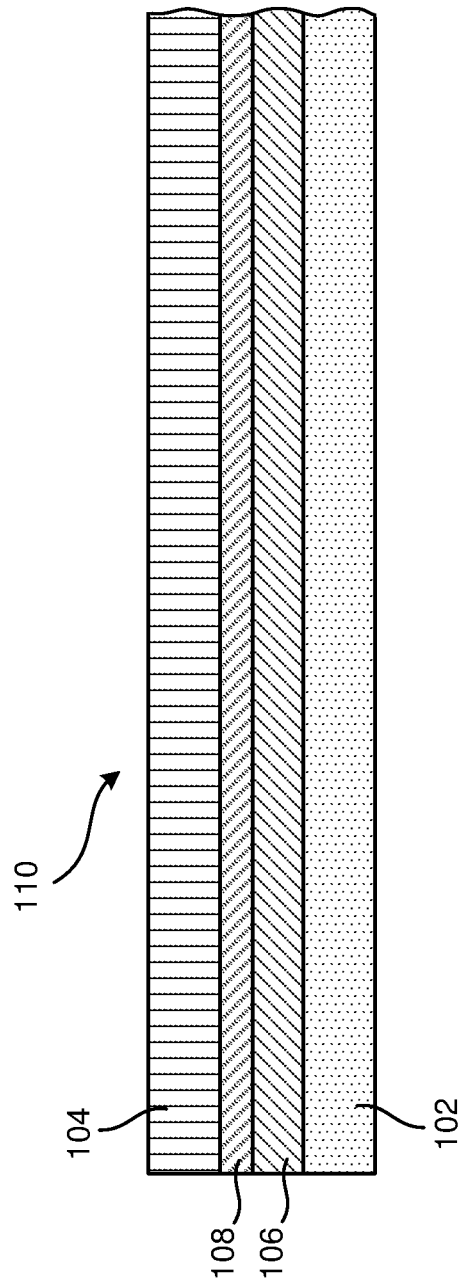
FIG. 2 is a cross sectional view of a seal portion of the package of FIG. 1, according to an embodiment of the present invention.
Figure 3:
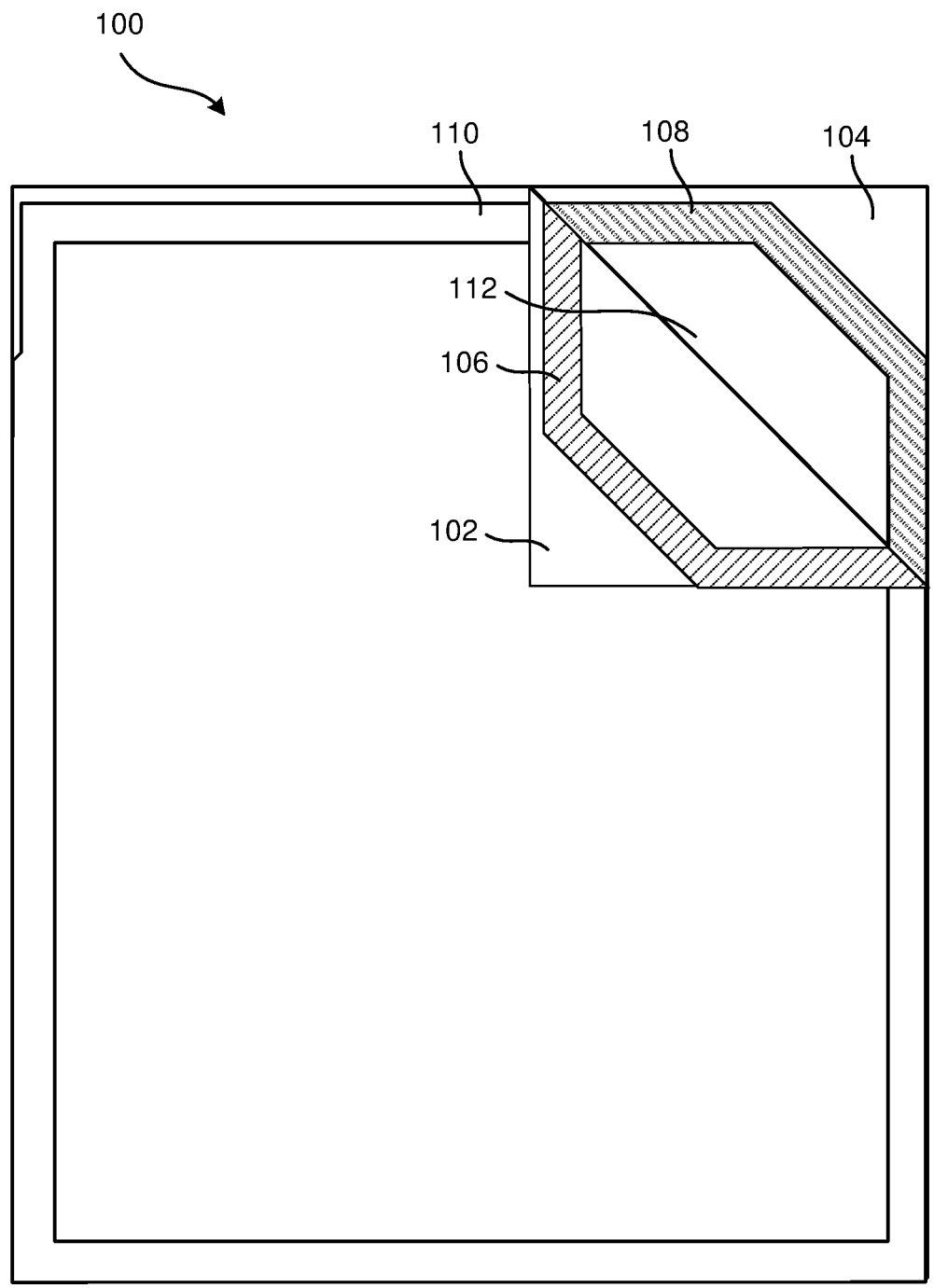
FIG. 3 is a side view of a package in an open configuration, according to an embodiment of the present invention.

Referring to FIGS. 1-3, a package 100 includes a first material 102, a second material 104, an adhesive layer 106, and a peel layer 108. A seal 110 is formed on at least a portion of a peripheral edge of the package 100 thereby creating the package 100 and forming an interior portion 112 of the package 100 where an object may be contained. The adhesive layer 106 and peel layer 108 can be coextruded, or can be extruded or manufactured separately using any of various known techniques, including but not limited to lamination, coating, or coextrusion. In an illustrative embodiment, the adhesive layer 106 and peel layer 108 are coextruded onto the first material 102, and the second material 104 is disposed on the peel layer 108. A seal between the peel layer 108 and the second material 104 is formed through heat sealing, ultrasonic sealing, or impulse sealing.

The first material 102 acts as a structural component and provides structure to the package 100. The first material 102 may be a film and can be made of any of various materials, including polymeric materials. In some examples, the first material 102 can be made of polyethylene, polyester, nylon, polypropylene, or any of various other polymer materials acting as a structural component of the package 100. In an example, the first material 102 may be transparent, allowing an object disposed in the package 100 to be visually identified while remaining sealed in the package 100. The first material 102 may also be first colored and/or adapted to provide ultraviolet protection to the object disposed in the package 100. In an example, the first material 102 may be transparent and have a color tint. The color tint may cooperate with a second color of the peel layer 108 to provide a third color for visual indication of the integrity of the seal 110 when the package 100 is in a closed or sealed configuration, thereby providing a visional indication that the package 100 is properly in the closed or sealed configuration.

The second material 104 also acts as a structural component and provides structure to the package 100. The second material 104 may be a non-woven material, such as non-woven high density polyethylene, which allows for the package to be breathable and gas sterilizable. In an example, the second material 104 can be uncoated Tyvek®, which allows the sealed package 100 (including an object disposed in the package 100) to be sterilized using ethylene oxide gas, as known in the art. For example, the non-woven material allows ethylene oxide gas to penetrate through the non-woven material and sterilize an object sealed in the package 100, and also allows the ethylene oxide gas to be evacuated through the non-woven material, resulting in a sterilized object sealed in the package 100.

The adhesive layer 106 is disposed on the first material 102. In an example, the adhesive layer 106 is sealed to the first material 102. The adhesive layer 106 may be made of any of various materials known in the art, such as low-density polyethylene, linear low density polyethylene, or any other polymer. In another example, the adhesive layer 106 may be a pressure-sensitive adhesive that allows the peel layer 108 to be decoupled and re-coupled to the adhesive layer 106. The adhesive layer 106 is preferably clear or colorless. However, in other examples, the adhesive layer 106 may include a colored dye or pigment.

The peel layer 108 is disposed on the adhesive layer 106. The peel layer 108 can be made of any of various materials or combinations of materials, for example, a blend of a base polymer (such as low-density polyethylene) and an incompatible polymer (such as polybutene). The incompatible polymer can weaken the bonds between the polymer chains to allow for easier separation of the peel layer 108 from the adhesive layer 106. In an example, the peel layer 108 is sealed to the adhesive layer 106, and is adapted to allow for a cohesive peel type seal between the peel layer 108 and adhesive layer 106. For example, the peel layer 108 and adhesive layer 108 may have a seal or peel strength of about 2 N/15 mm to about 5 N/15 mm, and more particularly about 3 N/15 mm to about 4 N/15 mm. Such a peel strength allows the package to be opened or disposed in an open configuration without substantially loosening or stressing fibers of the second non-woven material 104 and causing the second non-woven material 104 to tear. The peel layer 108 may also include a colored dye or pigment (forming a second color) that contrasts with the second material 104 and/or cooperates with the first color of the first material 102 to provide a visual indication of the integrity of the seal when the package 100 is in the closed or sealed configuration. Similarly, when the package 100 is in the open configuration, the peel layer 108 is substantially separated from the adhesive layer 106 and transferred to the second non-woven material 104. Thus, in the open configuration, the second color of the peel layer 108 is visible.

As mentioned above, the adhesive layer 106 and peel layer 108 may be coextruded, or can be extruded or manufactured separately using any of various known techniques. To form a sealed package 100, as illustrated in FIG. 1, the second non-woven material 104 is sealed to the peel layer 108 thereby forming the seal 110 including the first material 102, the adhesive layer 106, the peel layer 108, and the second non-woven material 104. The sealing of the package 100 may be accomplished via heat sealing. However, other methods may be used to seal the package 100, such as ultrasonic sealing or impulse sealing.

When the package 100 is in the closed configuration, the package 100 and an object disposed in the interior 112 of the package 100 can be sterilized using ethylene oxide gas, as known in the art. Alternatively, the object can be separately sterilized and sealed in the package 100 in a sterile environment.

Visual inspection of the seal 110 can be accomplished via inspection of the colored or pigmented peel layer 108 through the first material 102 and/or visual inspection of a cooperating color of the seal 110 formed by combination of a color of the first material 102 and a color of the peel layer 108. For example, the peel layer 108 may include a blue or other color dye or pigment, and the integrity of the seal 110 can be visually inspected to ensure no breaks or breaches of the colored peel layer 108 are present. In another example, the peel layer 108 may include a blue dye or pigment and the first material 102 may include a yellow tint that causes the seal 110 to have a green color.

When the package 100 is in the open configuration, the peel layer 108 substantially separates from the adhesive layer 106. Thus, the adhesive layer 106 remains coupled to the first material 102, and the peel layer 108 substantially transfers to the second non-woven material 104. For example, about 90% or more of the peel layer 108 transfers to the second non-woven material 104, while small amounts (such as about 10% or less) remain coupled to the adhesive layer 106. Further, the peel strength between the peel layer 108 and the adhesive layer 106 allows the package 100 to be opened or disposed in the open configuration without substantially loosening or stressing fibers of the second non-woven material 104 and causing the second non-woven material 104 to tear.

Figure 4:
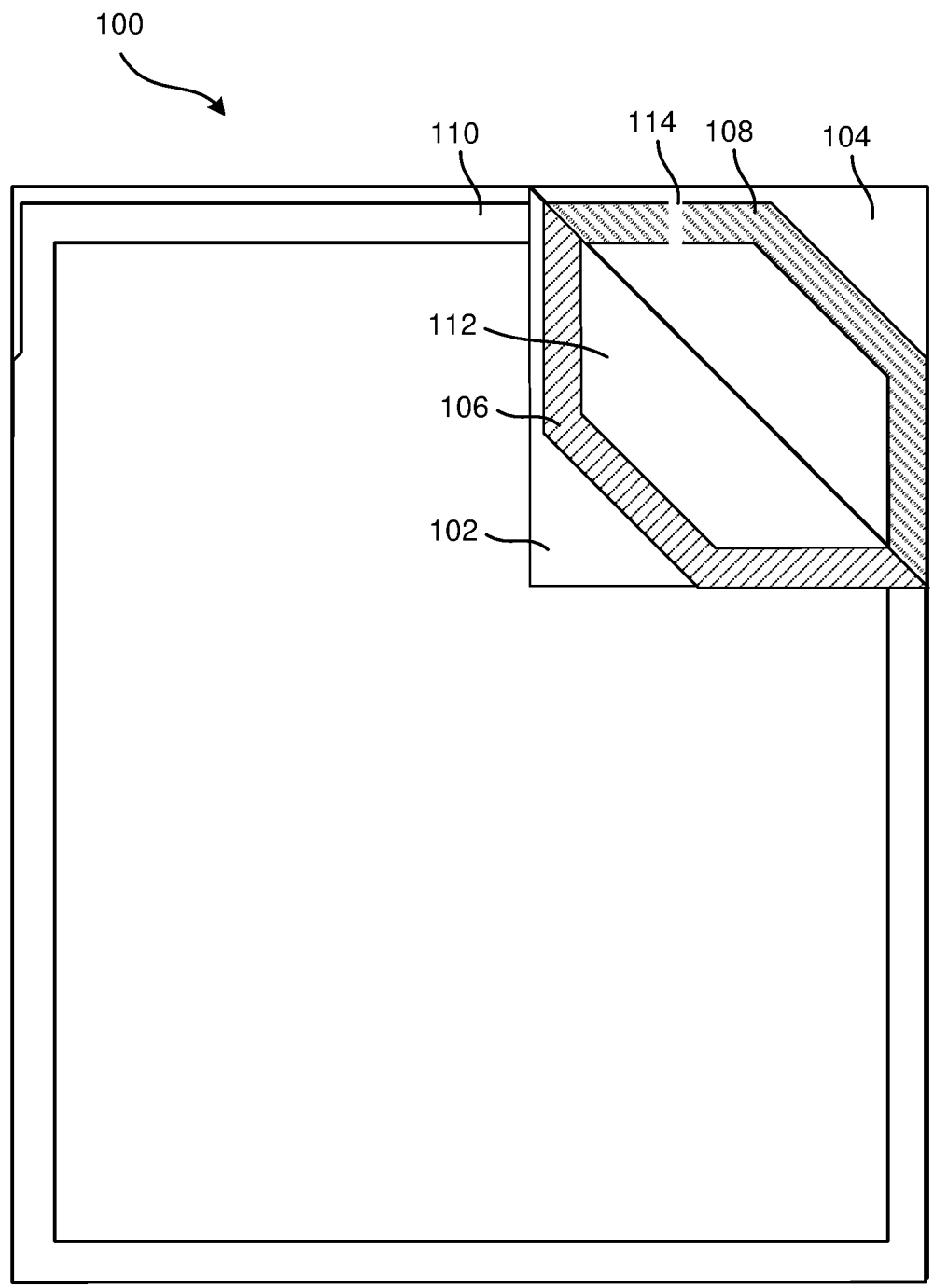
FIG. 4 is another side view of a package in an open configuration and illustrating a breach of the seal, according to an embodiment of the present invention.

In an example, in the open configuration, the first color of the first material 102 (e.g. yellow) and the second color of the peel layer 108 (e.g. blue) are individually visible, allowing for visual indication that the seal 110 has been opened. Visual inspection of the seal 110 can also be accomplished when the package is in the open configuration via inspection of the colored peel layer 108. In another example where the first material 102 is non-colored, the pigmented peel layer 108 coupled to the second non-woven material 104 can be inspected to ensure no breaks or breaches of the colored peel layer 108 are present. For example, as illustrated in FIG. 3, no breaks are present in the peel layer 108. In contrast, as illustrated in FIG. 4, an occlusion 114 is shown. This occlusion 114 visually indicates that the package 100 has been compromised or breached.

The techniques described above, including the seal 110 can be used in a tamper-evident package and the contents or objects of the package 100 can remain sterile until opened. Opening of the package 100 can be evident and visually indicated to the user through the use of a single color indication of the peel layer 108, or a color change indication caused by the colors of the peel layer 108 and the first material 102. The package 100 can include any of various colors, such as colors of a particular brand, hospital or any other color combination. Accordingly, branding can be applied to the package 100 and utilized for marketing purposes. Further, the shape of the package can be any shape. For example, the first material can be a cup, tray, flange, rim, board, base, shaft, or other structure.

As used herein, the term "coupled" and its functional equivalents are not intended to necessarily be limited to direct, mechanical coupling of two or more components. Instead, the term "coupled" and its functional equivalents are intended to mean any direct or indirect mechanical, electrical, or chemical connection between two or more objects, features, work pieces, and/or environmental matter. "Coupled" is also intended to mean, in some examples, one object being integral with another object. As used herein, the term "a" or "one" may include one or more items unless specifically stated otherwise.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of the inventors' contribution. The actual scope of the protection sought is intended to be defined in the following claims when viewed in their proper perspective based on the prior art.

What is claimed is:

1. A package having an open configuration and a closed configuration, the package comprising:
   first and second materials forming opposing sides of the package, wherein the second material is a non-woven material;
   an adhesive layer coupled to the first material; and
   a peel layer coupled to the adhesive layer and the non-woven material when the package is in the closed configuration, and has a seal strength between the adhesive layer and the peel layer of about 2 N/15 mm to about 5 N/15 mm, and wherein the peel layer is substantially separated from the adhesive layer and coupled to the non-woven material when the package is in the open configuration.

2. The package of claim 1, wherein the non-woven material is uncoated high density polyethylene.

3. The package of claim 1, wherein the adhesive layer is colorless, and the peel layer is colored.

4. The package of claim 1, wherein the peel layer is heat sealed to the adhesive layer.

5. The package of claim 1, wherein the first material has a first color.

6. The package of claim 5, wherein the peel layer has a second color.

7. The package of claim 6, wherein when the package is in the closed configuration, the first color and the second color cooperate and provide a third color that is visible.

8. The package of claim 7, wherein when the package is in the open configuration, the first color and the second color are individually visible.

9. A package having an open configuration and a closed configuration, the package comprising:
   first and second materials forming opposing sides of the package, wherein the second material is a non-woven material, and the first material has a first color; and
   a seal coupling the first and second materials together, and formed on at least a portion of a peripheral edge of the package, wherein the seal includes:
      an adhesive layer coupled to the first material; and
      a peel layer having a second color, wherein the peel layer is coupled to the adhesive layer and the non-woven material, and the first color and the second color cooperate and provide a third color when the package is in the closed configuration, and at least a portion of the peel layer is substantially separated from the adhesive layer and coupled to the non-woven material when the package is in the open configuration, and
      wherein a seal strength between the adhesive layer and the peel layer is about 2 N/15 mm to about 5 N/15 mm.

10. The package of claim 9, wherein the non-woven material is uncoated high density polyethylene.

11. The package of claim 9, wherein the first material is transparent, and the first color provides a first color tint.

12. The package of claim 9, wherein the adhesive layer is a pressure-sensitive adhesive that allows the peel layer to be decoupled and re-coupled to the adhesive layer.

13. A method, comprising:
   coextruding an adhesive layer and peel layer onto a first material, wherein the peel layer has a first color and the first material is transparent; and
   sealing a second material to the peel layer, wherein the first and second materials form opposing sides of a package, and the second material is a non-woven material,
   wherein a seal strength between the adhesive layer and the peel layer is about 2 N/15 mm to about 5 N/15 mm.

14. The method of claim 13, further comprising visually inspecting the seal by inspecting the first color of the peel layer through the first material for breaks.

15. The method of claim 13, wherein the first material has a second color, and the first color and the second color cooperate and provide a third color; and
   further comprising visually inspecting the seal by inspecting the third color through the first material for breaks.

16. The method of claim 13, further comprising disposing an object in an interior of the package.

17. The method of claim 16, further comprising sterilizing the package with the object in the interior of the package.

* * * * *